United States Patent [19]

Humenick

[11] Patent Number: Plant 6,805

[45] Date of Patent: May 16, 1989

[54] ROSE PLANT JACMUR

[75] Inventor: Muriel Humenick, Diamond Springs, Calif.

[73] Assignee: Jackson & Perkins Company, Medford, Oreg.

[21] Appl. No.: 139,210

[22] Filed: Dec. 29, 1987

[51] Int. Cl.[4] ..... A01H 5/00

[52] U.S. Cl. ..... Plt./14

[58] Field of Search ..... Plt./14

*Primary Examiner*—James R. Feyrer

*Attorney, Agent, or Firm*—Majestic, Parsons, Siebert & Hsue

[57] ABSTRACT

A rose variety of the hybrid tea class is provided having vigorous, well branched growth, an abundance of large, dark green, semi-glossy foliage with blooms of white (having a slight indication of yellow pigment) and very little fragrance, and with numerous stipitate glands on the edge and outer surface of sepals on the rachis.

1 Drawing Sheet

SUMMARY OF THE DISCOVERY

The present discovery relates to a new and distince variety of rose plant of the hybrid tea class, which I discovered in a cultivated area and I asexually reproduced. This new rose variety is a mutation of the rose plant designated "Pristine", which variety is described and illustrated in U.S. Plant Pat. No. 3,997, issued Dec. 21, 1976, inventor Warriner, incorporated herein by reference and of common assignment herewith.

The rose plant of the present discovery has a unique combination of characteristics which are outstanding in the new variety and which distinguish it from the rose plant Pristine, as well as from all other varieties of which I am aware. For example, this new rose variety has:

White buds and flowers with a slight indication of yellow pigment, rather than the pink areas on white buds and flowers of the Pristine variety.

Asexual reproduction of this new variety by budding, as performed at Wasco, Calif., shows that the foregoing characteristic and distinction comes true to form and is established and transmitted through succeeding propagation.

DESCRIPTION OF THE DRAWING

The accompanying illustration shows a typical bud and flower of this new variety and, for contrast, a typical bud and flower of the Pristine variety, depicted in color as nearly true as it is reasonably possible to make the same in a color illustration of this character.

DETAILED DESCRIPTION OF THE DISCOVERY

The following is a detailed description of my new rose variety, which has been denominated "JACMUR". Color terminology is in accordance with Wilson's Horticultural Color Chart except where an ordinary dictionary significance for the color is apparent or where reference is made to the Royal Horticultural Society Colour Chart.

Discovery of this mutation was in a cultivated area (a nursery) in Citrus Heights, Calif., and observations of the buds and flowers of the asexually reproduced plant were made in nurseries at Citrus Heights, Calif. and Irvine, Calif. Except as specifically indicated, the new rose variety is identical to the Pristine variety.

Flower

The blooming habit is continuous. The bud size is about one and one-half inches when the petals start to unfurl. The bud form is pointed ovoid with a broad base. By contrast to the Pristine variety, the bud color when sepals first divide is white; when half blown the upper side of petals is white, and the lower side of petals is white. The sepals have an outer surface color near Scheeles Green (860/3), usually heavily shaded with Garnet Brown (00918), numerous stipitate glands on edges and outer surface. Inner surface is near Scheeles Green (860/3), occasionally shaded with Garnet Brown (00918), and with a little white tomentum. Three appendaged sepals are lightly appendaged. Two unappendaged sepals are hairy edged. The receptacle color is near Scheeles Green (860/3) shaded with Garnet Brown (00918), of a funnel shape, large size and smooth surface. The peduncle is of medium to short length, slightly glandular surface. Peduncle color is bronzy, and the peduncle is stiff and erect. Petals show a slow recurving when opening.

Bloom

Bloom size is large, with an average open size of four and one-half to five and one-half inches, borne singly or several together. The stems are strong, and medium. The form when first open is high center. This form is retained to the end. Under normal conditions there are thirty to thirty-five petals. Unlike the Pristine variety, the upper side of petal at the flower center is white, as is the reverse side of the petals, with a slight indication of yellow pigment as indicated by a faint overlay of near Yellow Green Group 154D (The Royal Horticultural Society), especially at the base of the petals. The general tonality at the end of the first day shows no change in color. At the end of the third day, there remains no discoloration.

The fragrance is slight. The petal texture is thick and leathery, of a round shape and the tips are slightly recurved.

The arrangement is loosely imbricated with few petaloids in the center. The blooms drop off cleanly, and last both on the plant and as a cut flower for a long time.

Reproductive Parts

The anthers are medium size, of yellow color and arranged regularly around the styles. The filaments are near Rose Madder (23/1) in color. The pollen is lemon yellow, the styles along distal half are near Rose Madder (23/1) and along basal half near Primrose Yellow (601/2). Stigmas are yellow.

Plant

A very vigorous bush, with branching and being slightly sprawly.

Foliage

Very large to large size, abundant in quantity. The new foliage is near Garnet Brown (00918/3), and the old foliage is near Parsley Green (00962). Normal mid-stem leaves have five, and occasionally seven, leaflets.

The leaflets are of an oval pointed shape, the upper side of which are semi-glossy, and have a serrated edge. The serration is single and small in size. Petiole rachis is green with reddish markings near the axis and petiole underside has large prickles. There are many stipitate glands on all surfaces of rachis and the stipules are long and glandular edged. The foliage is resistant to mildew under normal growing conditions at Irvine, Calif.

Wood

New wood is near Garnet Brown (00918/3), with a smooth bark. Old wood is green with a smooth bark.

Prickles

There are many to an ordinary number of prickles on main canes from the base and on laterals from the main canes. The form is medium, broad based and hooked downward. Color when young is brown. The prickles are irregularly positioned.

Small Prickles

There are no small prickles on the main stalks or on the laterals.

Parentage

A color mutation of the Pristine variety.

Classification

Botanical is rosa hybrid. Commercial is hybrid tea.

I claim:

1. A new and distinct variety of rose plant and parts thereof of the hybrid tea class substantially as herein shown and described, characterized particularly as to novelty by the unique combination of its vigorous, well branched growth, an abundance of large, dark green, semi-glossy foliage with blooms of white having a slight indication of yellow pigment and very little fragrance, and with numerous stipitate glands on the edge and outer surface of sepals on the rachis.

* * * * *

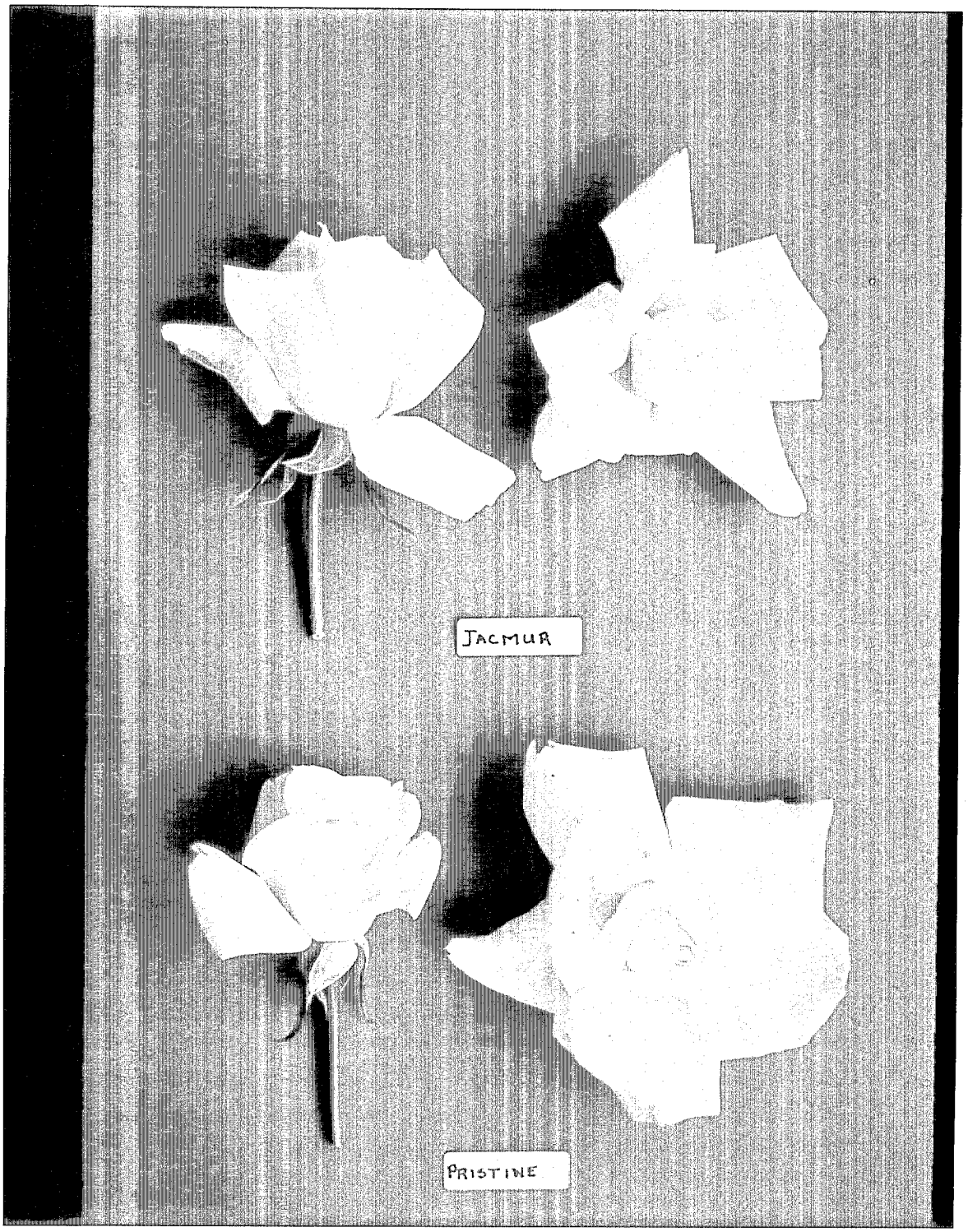
JACMUR
PRISTINE